US011305048B2

(12) United States Patent
Kilcran

(10) Patent No.: US 11,305,048 B2
(45) Date of Patent: Apr. 19, 2022

(54) ELECTRONIC VACUUM REGULATOR DEVICE

(71) Applicant: Medtec Medical, Inc, Buffalo Grove, IL (US)

(72) Inventor: Michael D. Kilcran, Antioch, IL (US)

(73) Assignee: Medtec Medical, Inc., Buffalo Grove, IL (US)

( * ) Notice: Subject to any disclaimer, the term of this patent is extended or adjusted under 35 U.S.C. 154(b) by 540 days.

(21) Appl. No.: 15/788,214

(22) Filed: Oct. 19, 2017

(65) Prior Publication Data

US 2018/0104390 A1 Apr. 19, 2018

Related U.S. Application Data

(60) Provisional application No. 62/409,952, filed on Oct. 19, 2016.

(51) Int. Cl.
| | |
|---|---|
| *A61M 35/00* | (2006.01) |
| *A61M 1/00* | (2006.01) |
| *G05D 16/20* | (2006.01) |
| *G05D 16/00* | (2006.01) |
| *A61M 3/00* | (2006.01) |
| *A61M 31/00* | (2006.01) |

(Continued)

(52) U.S. Cl.
CPC .......... *A61M 1/743* (2021.05); *A61M 1/0001* (2013.01); *A61M 1/734* (2021.05); *A61M 1/74* (2021.05); *G05D 16/024* (2019.01); *G05D 16/2013* (2013.01); *A61M 2202/04* (2013.01); *A61M 2205/18* (2013.01); *A61M 2205/3334* (2013.01); *A61M 2205/3393* (2013.01); *A61M 2205/3553* (2013.01); *A61M 2205/50* (2013.01); *A61M 2205/505* (2013.01)

(58) Field of Classification Search
CPC .......... A61M 35/00; A61M 1/00; A61M 3/00; A61M 31/00; A61M 2202/04; A61M 2205/18; A61M 2205/3334; A61M 2205/3393; A61M 2205/3553; A61M 2205/50; A61M 2205/505; A61F 13/00; A61F 13/02; A61F 8/44

See application file for complete search history.

(56) References Cited

U.S. PATENT DOCUMENTS

| | | | |
|---|---|---|---|
| 5,636,643 A | 6/1997 | Argenta et al. | |
| 7,022,113 B2 * | 4/2006 | Lockwood | A61M 1/732 604/313 |
| 7,553,306 B1 | 6/2009 | Hunt et al. | |

(Continued)

FOREIGN PATENT DOCUMENTS

| | | |
|---|---|---|
| CN | 2082172 U | 8/1991 |
| CN | 102430158 A | 5/2012 |

(Continued)

*Primary Examiner* — Michele M Kidwell
*Assistant Examiner* — Ilya Y Treyger
(74) *Attorney, Agent, or Firm* — Price Heneveld LLP

(57) ABSTRACT

A vacuum regulator device having a vacuum regulator and a vacuum gauge on a housing line that is configured to be in fluid communication with a patient include an electronic valve that selectively opens and closes the housing line. The vacuum gauge is located between the vacuum regulator and the patient and includes an electronic flow sensor upstream. The electronic flow sensor provides feedback to the vacuum regulator.

18 Claims, 4 Drawing Sheets

(51) Int. Cl.
    *A61F 13/00*        (2006.01)
    *A61F 13/02*        (2006.01)

(56)            References Cited

U.S. PATENT DOCUMENTS 7,651,484  B2     1/2010  Heaton et al.
    7,779,625  B2     8/2010  Joshi et al.
    9,526,816  B2 *  12/2016  Toth .................... A61M 1/0031
   10,485,906  B2 *  11/2019  Freedman ............. A61M 37/00
 2002/0173705  A1    11/2002  Jones et al.
 2002/0173706  A1    11/2002  Jones et al.
 2008/0105058  A1     5/2008  Krupa et al.
 2009/0312725  A1    12/2009  Braga
 2013/0267919  A1    10/2013  Caso et al.
 2016/0184496  A1     6/2016  Jaecklein et al.

FOREIGN PATENT DOCUMENTS

CN        102743800  A     10/2012
    CN        102085398  B      8/2013
    CN        103930138  A      7/2014
    CN        204501835  U      7/2015
    CN        103182102  B      3/2016
    CN        205322866  U      6/2016
    EP          2782615  B1    11/2012
    WO       2009021047  A2     2/2009

* cited by examiner

ELECTRONIC VACUUM REGULATOR DEVICE

CROSS-REFERENCE TO RELATED APPLICATIONS

This application claims priority under 35 U.S.C. 119(e) to U.S. Provisional Patent Application No. 62/409,952, filed Oct. 19, 2016, entitled "ELECTRONIC VACUUM REGULATOR DEVICE," which is herein incorporated by reference in its entirety.

FIELD OF THE INVENTION

The present disclosure relates to vacuum regulators that are used to withdraw fluids from a patient.

BACKGROUND OF THE INVENTION

Vacuum withdrawal systems are used in a hospital setting to withdraw fluids from a cavity of a patient. Hospitals typically have a central vacuum source on site, and a series of lines from the central vacuum source to various operating rooms and patient rooms throughout the hospital. In these rooms, a vacuum regulator is attached to the central vacuum source, typically at a wall connection, to provide a regulated source of vacuum to the patient. Specifically, the vacuum regulators are used to regulate for a specific level of vacuum pressure that is established by the caregiver. The level of the vacuum applied to the patient can be changed by resetting the vacuum regulator. To modify the vacuum regulator setting, typically the caregiver manually rotates an actuator or control knob on the vacuum regulator. A vacuum gauge provides a visual indication of the vacuum level.

From the central vacuum source, hospital full wall vacuum may exceed 635 mmHG, and is often around 444 mmHG. Depending on the treatment of the patient and the condition of the patient, a lower vacuum level may be required. A maximum threshold level of vacuum can be set by the caregiver to suppress the vacuum level to a level of vacuum that is lower than full wall vacuum. This is done by the caregiver setting a maximum level of vacuum that can be applied to the patient. When setting a maximum level of vacuum, the vacuum system must be at a "no flow" condition to get an accurate reading. A "no flow" condition is normally achieved by the caregiver turning on the regulator to draw fluid, and occluding the line on the upstream side of the vacuum regulator, i.e. between the regulator and the patient. Occluding the line is achieved by the caregiver clamping the line between their fingers or using a clamping device. While the line is occluded, the vacuum regulator dial is manually manipulated until the vacuum gauge hits the desired maximum vacuum level as specified by the caregiver. Thereafter, the occlusion from the line can be removed and the vacuum regulator can be applied to a patient.

Thus, the prior art vacuum withdrawal systems are all mechanical in nature, and require competing tasks of the caregiver to set the vacuum to the appropriate level. Setting the maximum vacuum level requires the caregiver to perform multiple activities at once, including occluding the line, turning the control knob, and monitoring the regulator gauge. To further complicate operation of the vacuum system, often a patient's treatment requires tapering maximum levels of vacuum pressure.

Further, in current vacuum withdrawal systems, when the vacuum level exceeds or drops out of a prescribed range for a particular patient, the caregiver must rely on a visual inspection of the regulator gauge, a comparison of prescribed ranges, and react accordingly to reestablish the prescribed vacuum level.

Withdrawn fluids from the patient, called exudate, are collected in a canister. Another drawback of current vacuum withdrawal systems is that the caregiver must monitor the level of the exudate in the canister to avoid overfilling.

A trap is typically located between the canister and the vacuum regulator, and prevents the exudate from entering the vacuum regulator. However, a further drawback of current vacuum withdrawal systems is that the caregiver must visually inspect whether the trap has been contaminated with exudate.

Accordingly, there are many competing demands placed on the caregiver while operating a vacuum withdrawal system to aspirate a patient.

SUMMARY OF THE INVENTION

A vacuum regulator device includes a vacuum line having a proximal end and an open distal end, a vacuum regulator in fluid communication with the vacuum line and regulating fluid flow through the vacuum line to an adjustable pressure level, and a vacuum gauge in communication with the vacuum line between distal end and the vacuum regulator and in electronic communication with the vacuum regulator.

A vacuum withdrawal system includes a vacuum regulator device, a fluid vessel upstream of the regulator device, a sensor proximate the fluid vessel, and an alarm in electronic communication with the sensor and outputting an alarm upon fluid entering the trap, as detected by the sensor.

A vacuum withdrawal system includes a vacuum regulator device. The vacuum regulator device includes a vacuum line having a proximal end and an open distal end, a vacuum regulator in fluid communication with the vacuum line and regulating fluid flow through the vacuum line to an adjustable pressure level, and a vacuum gauge in communication with the vacuum line between distal end and the vacuum regulator and in electronic communication with the vacuum regulator. The vacuum withdrawal system further includes a fluid vessel upstream of the regulator device, a sensor proximate the fluid vessel, an alarm in electronic communication with the sensor and outputting an alarm upon fluid entering the trap, as detected by the sensor, and a housing enclosing the vacuum regulator and the vacuum gauge, the vacuum line extending from the housing, and the vessel and sensor being mounted on the housing.

Further objects and advantages of the invention will be apparent from the drawings and the following detailed description of preferred embodiments.

DETAILED DESCRIPTION

Figure 1:
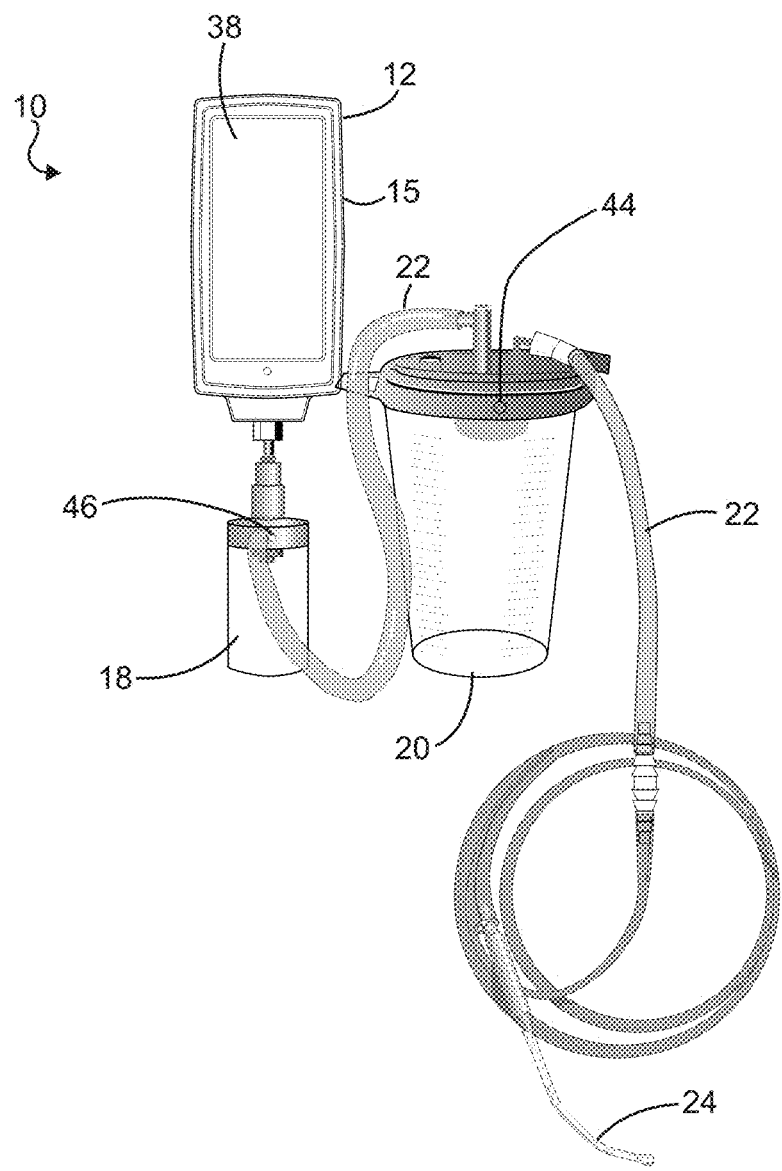
FIG. 1 is a perspective view of a vacuum withdrawal system of the present invention.
Figure 2:
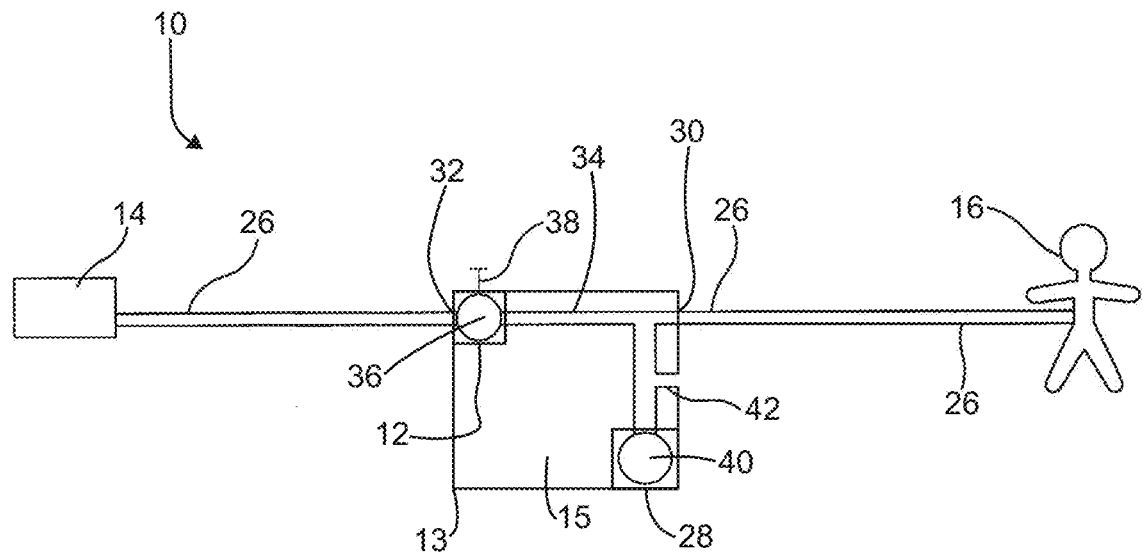
FIG. 2 is a schematic view of the vacuum withdrawal system of FIG. 1 in fluid communication with a vacuum source.
Figure 3:
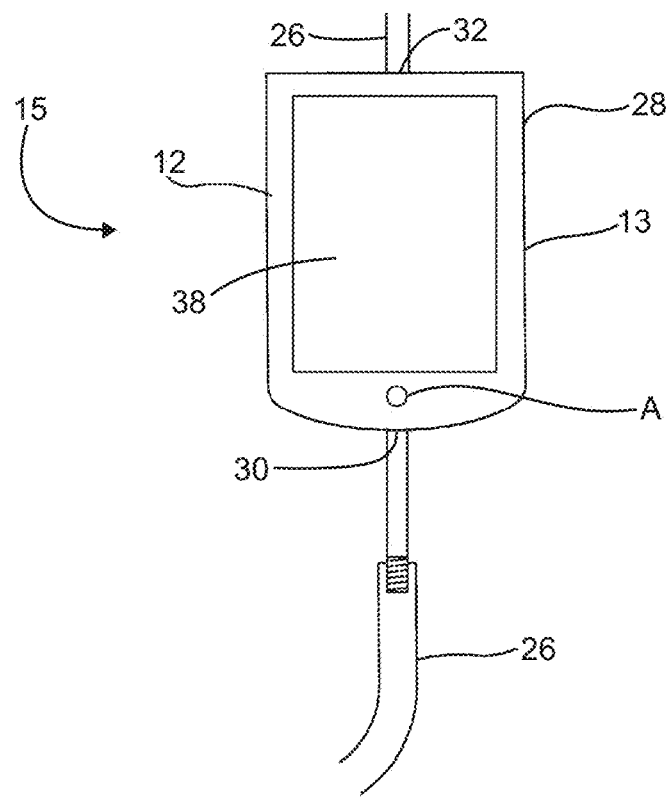
FIG. 3 is a front view of one embodiment of a vacuum regulator device including a vacuum regulator and a vacuum gauge.
Figure 4:
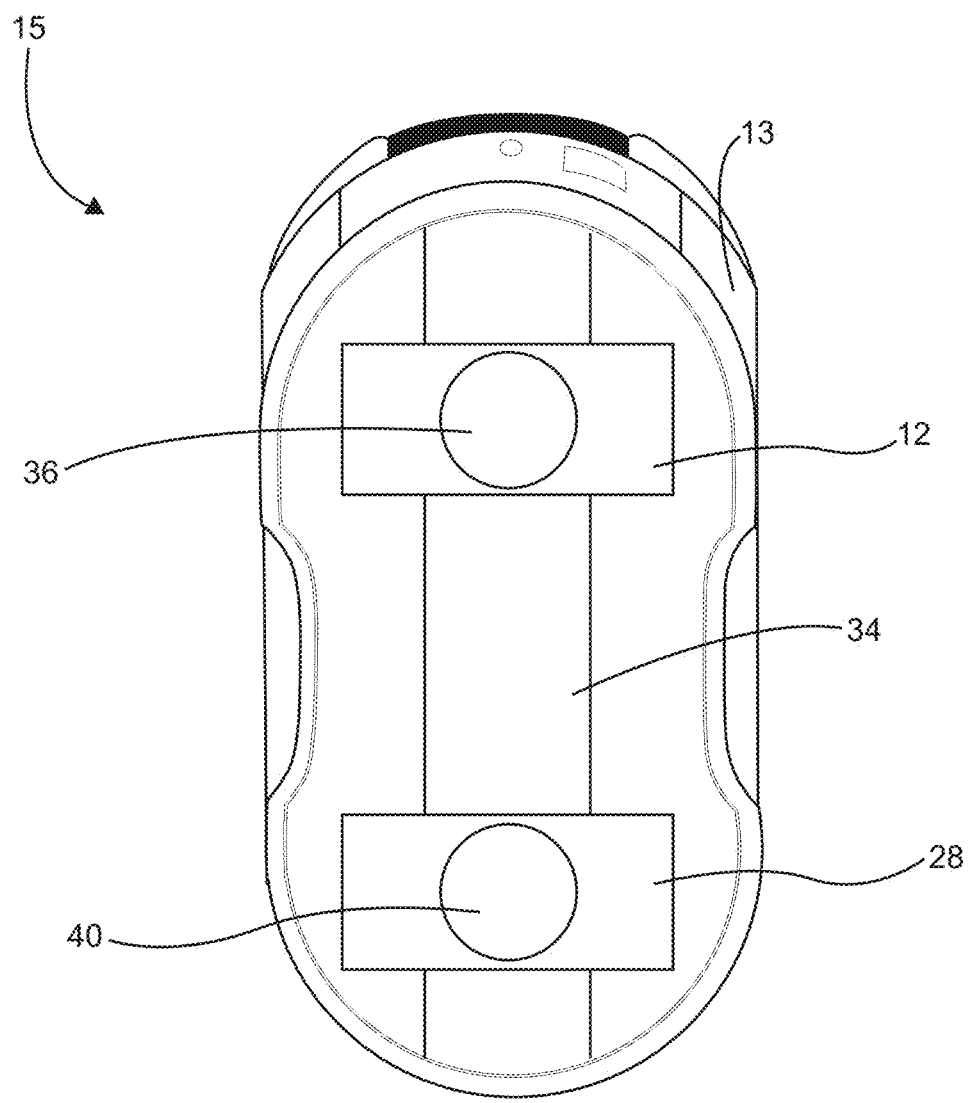
FIG. 4 is a schematic of an electronic valve and an electronic sensor of the vacuum regulator device.
Figure 5:
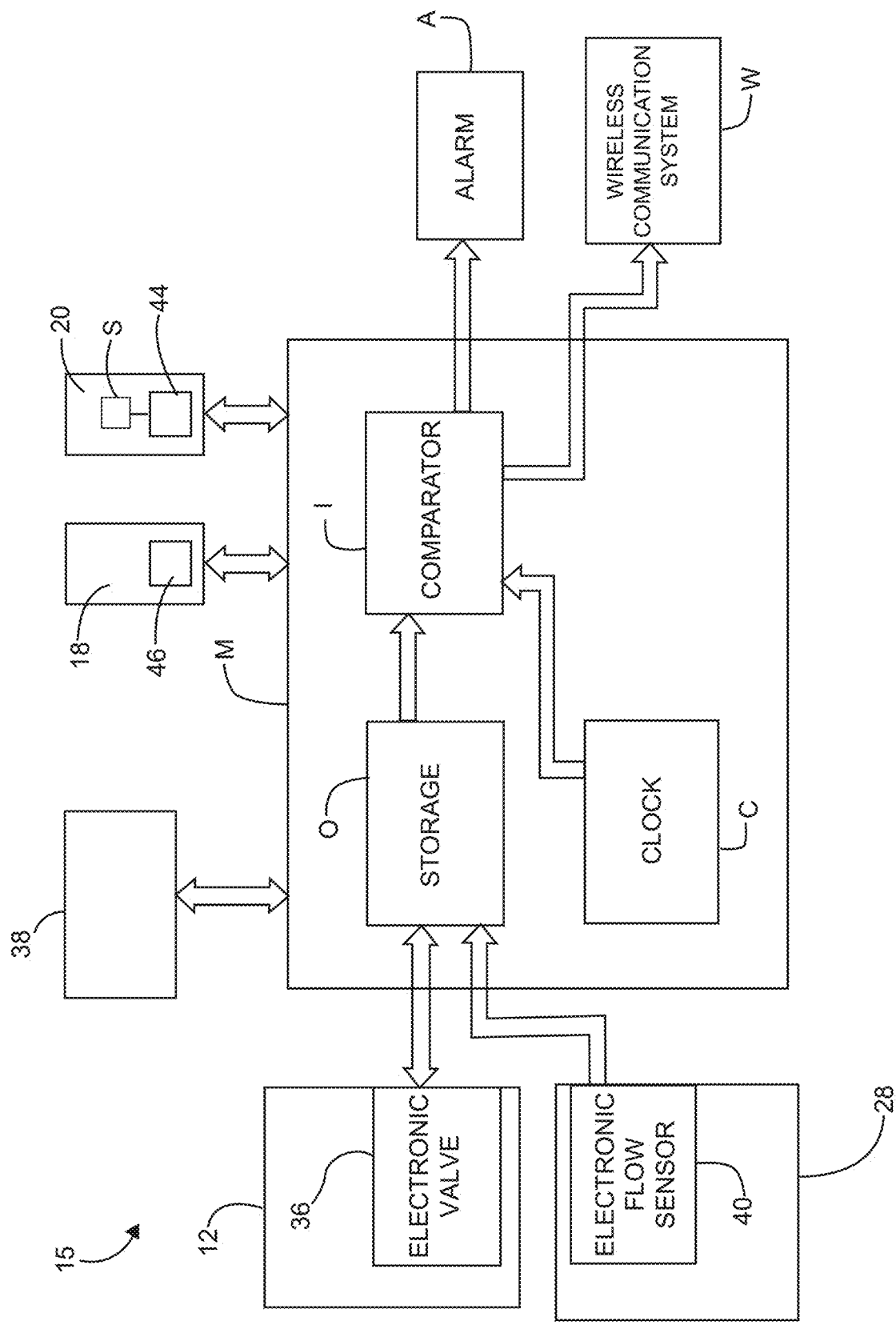
FIG. 5 is a block diagram of the communication between components of the vacuum regulator device and their connection to a microprocessor.

Referring to FIGS. 1 and 2, a vacuum withdrawal system is indicated generally at 10, and includes a vacuum regulator 12 that is attached upstream of the central vacuum source 14 (seen in FIG. 2) to provide a regulated source of vacuum to the patient 16 (also seen in FIG. 2). As used herein, the source of vacuum will be a downstream location and the patient cavity will be an upstream location, such that the terms "upstream" and "downstream" will reference the flow of fluid in the direction from the patient 16 toward the central vacuum source 14.

As seen in FIG. 1, upstream of the vacuum regulator 12 is a trap 18 that prevents exudate from entering the vacuum regulator, and upstream of the trap is a collection canister 20 that receives and collects the exudate from the patient 16. Connection tubing 22 connects the trap 18 and the collection canister 20, such that they are in fluid communication. Upstream of the collection canister 20 is a suction device 24, such as a cannula, catheter, tube or other device, which is introduced into the patient 16 for withdrawing the fluids that are collected in the collection canister.

Turning now to FIG. 2, a schematic view of a vacuum withdrawal system 10 includes the vacuum source 14, which is a centrally located supply of vacuum that is communicated to various rooms throughout the hospital on a vacuum line 26. It is contemplated that other sources of vacuum 14 can be used, such as a portable unit. At the room, the caregiver plugs in the vacuum withdrawal system components 10 shown in FIG. 1 to fluidly communicate with a patient 16. The vacuum line 26 communicates between that vacuum source 14 and the patient 16, and may comprise multiple vacuum lines and multiple connection tubes 22 in series communication with each other.

Turning now to FIGS. 1-4, a vacuum gauge 28 is preferably contained within a common housing 13 with the vacuum regulator 12 forming a regulator device 15, which has an inlet port 30 and an outlet port 32. The outlet port 32 is formed in the common housing 13 and is the downstream end of the vacuum regulator that is adapted to be connected to the vacuum source (see FIG. 2). The inlet port 30 is also formed in the housing 13 and is adapted to be connected to the upstream vacuum line 26 that extends towards the patient 16. A housing line 34 is in fluid communication between in the inlet port 30 and the outlet port 32, and the vacuum gauge 28 is upstream of the vacuum regulator 12 on the housing line 34. The vacuum regulator 12 sets the vacuum level that reaches the patient 16 and is adjusted by the caregiver.

The vacuum regulator 12 comprises an electronic valve 36 that is movably retained within the housing 13 such that the valve can variably seal-off, open and partially open the housing line 34 to effect a change in the vacuum level at the patient 16.

The electronic valve 36 can be used to entirely occlude the housing line 34 to shut-off the vacuum line and achieve the "no flow" condition through the vacuum regulator. Electronic valves, such as those commercially available from Koge Micro Tech Co., Equilibar, and MTI, may be used.

The electronic valve 36 is controlled by the caregiver with an input/output device, such as a touch screen 38, on the exterior surface of the housing 13. With a touch screen 38, the caregiver can input a level of flow through the electronic valve 36. It is also contemplated that the touch screen 38 can output or display a value indicating the current position or level of occlusion of the housing line 34 by the electronic valve 36.

The vacuum gauge 28 indicates of the level of the vacuum flow that is being applied to the patient 16. The vacuum gauge 28 includes an electronic flow sensor 40 that is located upstream of the vacuum regulator 12 so that it reads the level of vacuum where the vacuum level is being applied to the patient 16. Electronic flow sensors, such as those commercially available from MKS Instruments or Koge Micro Tech Co., may be used. A bleed orifice 42 is also provided in vacuum line to the vacuum gauge 28 for the vacuum gauge to read the level of that vacuum to the patient. Alternatively, a transducer can be used to sense the vacuum flow upstream of the vacuum regulator 12. It is contemplated that the vacuum gauge 28 displays the vacuum flowrate at the touch screen 38.

When the caregiver is setting the vacuum level, the caregiver can inspect the touch screen 38 of the vacuum gauge and set the vacuum regulator via touch-screen to the desired level of vacuum to be applied to the patient 16. Further, when the caregiver wants to establish or change a setting of the level of vacuum applied to a patient 16, the caregiver can input the change via the touch-screen 38, and the electronic valve 36 automatically opens or closes the vacuum line to varying degrees. The electronic flow sensor 40 provides feedback to indicate the vacuum level at the touch screen 38.

The input/output device 38 is preferably a touch-screen, however other interfaces are contemplated. The touch screen 38 is preferably a Liquid Crystal Display (LCD), and more preferably the touch screen is backlit for a dimly-lit environment. It is possible that the touch screen 38 may be programmed to turn-off within certain amount of time, for example 5-mins after operation of the vacuum regulator device 15.

The electronic valve 36 can be operated based on feedback from the electronic flow sensor 40. The regulator device 15 includes a microprocessor M having a memory storage O to store data the readings from the electronic flow sensor 40 and/or the readings from the electronic valve 36. The memory storage O, a clock C and a comparator I allow the microprocessor M to be programmed to operate the regulator device 15 under prescribed ranges of flow for prescribed durations of time. In one embodiment, the microprocessor M may be programmed to automatically operate at differing flow levels over time, for example 66 mmHG for 5 minutes followed by 75 mmhg for 10 minutes, and may include a range of preset flows or a range of flows dictated by caregiver. The microprocessor M may automatically shut-off the regulator device 15 when vacuum levels exceed or drop below a certain range, or alternatively, the microprocessor may hold the vacuum flow at the outer limits of the prescribed range. The microprocessor M may have programmable settings or presets that are associated with certain types of aspiration procedures or for certain types of patients. The microprocessor M also allows for storage of historical data and calibration between the electronic flow sensor 40 of the vacuum gauge 28 and the electronic valve 36 of the vacuum regulator 36. It is also contemplated that the microprocessor M can be located remotely to the housing 13.

The regulator device 15 is preferably provided with an alarm A that is responsive to signals generated by the electronic flow sensor 40 and/or the electronic valve 36. The alarm A may be an audible alarm and/or a visual alarm, such as an LED on the regulator device 15, or alternatively a display on the touch screen 38. Conditions in which the alarm A might be initiated are when the flow level is out of a prescribed range, or when there is no flow. For example, when the vacuum levels are not within prescribed range as stored in the memory storage O of the microprocessor M, or not within a prescribed time-period as compared at a comparator I with a clock C, an audible alarm and/or visual indicator is initiated. When the condition is corrected and levels return to within the prescribed parameters, the alarm A will automatically cease. It is contemplated that the alarm A can be located either or both upstream or downstream of the electronic valve 36 for indicating low volume and/or low pressure conditions.

A wireless communication system W connects the regulator device 15 to broadcast the flow rate in real time, and in particular, any alarm conditions, to remote locations. Examples of such remote locations include the nurses station in a hospital setting, as well as to home care providers. The wireless communication system W can be integrated with an existing hospital alarm system, and with health records systems. The wireless communication system W can also be used to communicate with personal devices of health care providers, such as cell phones, pagers, tablets and other personal computers. The wireless communication system W may be a Wi-Fi or BLUETOOTH® system, however other systems are contemplated.

It is contemplated that the vacuum regulator device 15 can operate in two automatic modes: "Respiratory mode" and "Wound Vac mode". Selection between the two modes can be made by selection of a corresponding icon on the touch screen 38.

Typically, a separate pump is used to create negative pressure for wound therapy (NPWT) due to the potential adverse effects of the use of high pressure hospital wall vacuum on sensitive, chronic wound tissue. However, with the precision that the vacuum regulator device 15 provides, hospital wall gas can be used for NPWT in the "Wound Vac mode". Within the "Wound Vac mode", one or more pre-set settings are available to the user, for example selection between 75 mmHG, 100 mmHG, or 125 mm/HG. Alternatively, or in combination with the pre-set settings, the level of pressure can be fully selectable by the user between low flow and low pressure levels of 75 mmHG and 150 mmHG. The "Wound Vac mode" can also deliver continuous or intermittent pressures. In contrast, the "Respiratory mode" can operate at any flow and pressure settings, and continuous or intermittent pressures.

It is contemplated that the regulator device 15 is powered by mains power, battery power, solar power, and/or an in-line turbine, among other power sources.

Withdrawn fluids from the patient, called exudate, are collected in the canister 20. When the canister 20 is full of exudate such that fluid reaches the top surface of the canister, an alarm condition is communicated to an alarm 44 that is powered by a coin cell battery. In one example, canister 20 can include sensor S adjacent an upper portion thereof to send a signal to microprosessor M, or another output directly, when canister 20 is full or near-full. In particular examples, a photo cell, a float connected with a mechanical switch or the like can be used for sensor S. In this manner, the fluid within the canister 20 completes a circuit, resulting in an audible alarm or visual indicator such as an LED 44. It is possible that the alarm 44 is displayed at the touch screen 38 of the regulator device 15.

It is also contemplated that the weight of the exudate in the canister 20 is determined with a scale, which may be integral with the canister or provided at a mounting point between canister and housing 13. The weight is communicated from the scale to the microprocessor M, for example, which uses the weight of the fluid with other data, for example the time over which it is extracted and the pressure with which it is extracted, to calculate estimated characteristics of the wound. For example, characteristics such as the volume of the wound, the amount of fluid withdrawn over time, and other characteristics of the wound can be determined or estimated using data communicated to the microprocessor M.

The trap 18 is typically located between the canister 20 and the vacuum regulator 12, and prevents the exudate from entering the vacuum regulator device 15. If the trap 18 is contaminated with exudate, this condition is indicated at an alarm 46, such as LED on the trap and/or displayed at the touch screen 38 at the regulator device 15. It is contemplated that the alarm 46 is powered by a battery, such that when the trap 18 is contaminated by exudate, the moisture completes a circuit that communicates the condition to the alarm. It is also contemplated that the trap 18 is disposable after use.

With the regulator device 15, it is preferred that all exterior surfaces are treated with an anti-microbial agent, such as MicrobeCare™, quaternary ammonium antimicrobials, heavy metals such as silver and copper, poisons such as chlorhexidine (CHG), biguanides and Triclosan.

Since modifications within the spirit and scope of the invention may readily be effected by persons skilled within the art, it is to be understood that this invention is not limited to the particular embodiments described by way of example hereinabove. In the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

REFERENCE NUMBERS IN THE DRAWINGS

10 Vacuum withdrawal system
12 Regulator
13 Housing
14 Vacuum source
15 Regulator device
16 Patient
18 Trap
20 Collection canister
22 Connection tubing
24 Suction device
26 Vacuum line
28 Vacuum gauge
30 Inlet port
32 Outlet port
34 Housing line
36 Electronic valve
38 Input-output device/touch screen
40 Electronic flow sensor
42 Bleed Orifice
44 Canister Alarm
46 Trap Alarm
M Microprocessor
C Clock
I Comparator
A Alarm
W Wireless Communication System
S Canister sensor
O Storage

The invention claimed is:

1. A vacuum regulator device, comprising:
a vacuum line having a proximal end and an open distal end;
a vacuum regulator in fluid communication with the vacuum line and electronically adjustable to regulate fluid flow through the vacuum line;
a vacuum gauge in communication with the vacuum line between distal end and the vacuum regulator and in electronic communication with the vacuum regulator;
a controller programmed to execute a process for electronic adjustment of the vacuum regulator including receiving a user-selected pressure level within a range of pressure levels and causing electronic adjustment of the vacuum regulator such that a measured pressure level from the vacuum gauge, received by the controller, generally matches the user-selected pressure level; and
an input-output interface presenting a reading from the vacuum gauge and including an alarm indicating operation of the vacuum regulator outside of predetermined parameters.

2. The vacuum regulator device of claim 1, wherein the vacuum regulator includes an electronic valve in communication with at least one of the vacuum line and the vacuum regulator and selectively opening and closing fluidic communication to the vacuum line under control of the controller for electronic adjustment of the vacuum regulator.

3. The vacuum regulator device of claim 2, wherein the vacuum line is located upstream of the vacuum regulator.

4. The vacuum regulator device of claim 1, further including an outlet port in fluid communication with the vacuum regulator and configured for attachment with a vacuum source port.

5. The vacuum regulator device of claim 1, wherein the vacuum gauge is used in a feedback control scheme executed by the controller for electronic adjustment of the vacuum regulator such that the measured pressure level from the vacuum gauge generally matches the user-selected pressure level.

6. The vacuum regulator device of claim 5, further wherein the controller is a microprocessor in electronic communication with the vacuum gauge and the vacuum regulator and programmed to implement the feedback control scheme by obtaining the measured pressure level from the vacuum gauge and adjusting the vacuum regulator.

7. The vacuum regulator device of claim 1, wherein the vacuum gauge includes an electronic flow sensor.

8. The vacuum regulator device of claim 1, wherein
the input-output interface further includes an input for receiving a user-selected target pressure level.

9. The vacuum regulator device of claim 1, wherein:
the user-selected pressure level is a first pressure level;
the controller is further programmed to execute the process for electronic adjustment of the vacuum regulator including causing electronic adjustment of the vacuum regulator such that the measured pressure level from the vacuum gauge generally matches the first user-selected pressure level for a first time interval and causing electronic adjustment of the vacuum regulator such that the measured pressure level from the vacuum gauge generally matches a second user-selected pressure level for a second time interval; and
the input-output interface further includes an input for receiving a user-selection of one of a plurality of preset modes, including associated values for the first and second time intervals.

10. The vacuum regulator device of claim 1, further including:
a housing enclosing the vacuum regulator and the vacuum gauge; and
a touchscreen mounted with the housing and in communication with the vacuum gauge and the vacuum regulator for receiving a user input indicating the user-selected pressure level and displaying at least one of the user selected pressure level or the measured pressure level.

11. The vacuum regulator device of claim 1, further including an alarm in communication with the controller, the controller being configured for causing the alarm to provide an indication to a user that a fluid flow through the vacuum line is outside a predetermined range via the alarm.

12. A vacuum regulator device, comprising:
a vacuum line having a proximal end and an open distal end;
a vacuum regulator in fluid communication with the vacuum line and electronically adjustable to regulate fluid flow through the vacuum line;
a vacuum gauge in communication with the vacuum line between distal end and the vacuum regulator and in electronic communication with the vacuum regulator;
an input-output interface presenting a reading from the vacuum gauge and an input for receiving a user-selection of one of a plurality of preset modes, including associated values for a first user-selected pressure level within a range of pressure levels, a second user-selected pressure level, a first time interval, and a second time interval; and
a controller programmed to execute a process for electronic adjustment of the vacuum regulator including causing electronic adjustment of the vacuum regulator such that a measured pressure level from the vacuum gauge, received by the controller, generally matches the user-selected pressure level for the first time interval and causing electronic adjustment of the vacuum regulator such that the measured pressure level from the vacuum gauge generally matches the second user-selected pressure level for the second time interval.

13. The vacuum regulator device of claim 12, wherein the vacuum regulator includes an electronic valve in communication with at least one of the vacuum line and the vacuum regulator and selectively opening and closing fluidic communication to the vacuum line under control of the controller for electronic adjustment of the vacuum regulator.

14. The vacuum regulator device of claim 13, wherein the vacuum line is located upstream of the vacuum regulator.

15. The vacuum regulator device of claim 12, further including an outlet port in fluid communication with the vacuum regulator and configured for attachment with a vacuum source port.

16. The vacuum regulator device of claim 12, wherein the vacuum gauge is used in a feedback control scheme executed by the controller for electronic adjustment of the vacuum regulator such that the measured pressure level from the vacuum gauge generally matches the user-selected pressure level.

17. The vacuum regulator device of claim 16, further wherein the controller is a microprocessor in electronic communication with the vacuum gauge and the vacuum regulator and programmed to implement the feedback control scheme by obtaining the measured pressure level from the vacuum gauge and adjusting the vacuum regulator.

18. The vacuum regulator device of claim 12, wherein the vacuum gauge includes an electronic flow sensor.

* * * * *